US 9,571,121 B2

(12) United States Patent
Press et al.

(10) Patent No.: US 9,571,121 B2
(45) Date of Patent: Feb. 14, 2017

(54) ELECTROCHEMICAL SENSING MODULE

(71) Applicant: Atlas Scientific LLC, Brooklyn, NY (US)

(72) Inventors: Efrem Press, Brooklyn, NY (US); Jon Lindgren, Brooklyn, NY (US); Jordan Press, Brooklyn, NY (US)

(73) Assignee: ATLAS SCIENTIFIC LLC, Brooklyn, NY (US)

( * ) Notice: Subject to any disclaimer, the term of this patent is extended or adjusted under 35 U.S.C. 154(b) by 0 days.

(21) Appl. No.: 14/806,079

(22) Filed: Jul. 22, 2015

(65) Prior Publication Data

US 2016/0028414 A1 Jan. 28, 2016

Related U.S. Application Data

(60) Provisional application No. 62/028,469, filed on Jul. 24, 2014.

(51) Int. Cl.
*H03M 3/00* (2006.01)
*G01N 27/416* (2006.01)
*G01R 19/00* (2006.01)

(52) U.S. Cl.
CPC ......... *H03M 3/464* (2013.01); *G01N 27/4167* (2013.01); *H03M 3/476* (2013.01); *H03M 3/49* (2013.01); *H03M 3/494* (2013.01); *G01R 19/0023* (2013.01)

(58) Field of Classification Search
CPC .. H03M 1/0682; H03M 1/1295; H03M 1/745; H03M 1/181; H03M 1/44
USPC .......................................... 341/143, 144, 155
See application file for complete search history.

(56) References Cited

U.S. PATENT DOCUMENTS

| | | | | | |
|---|---|---|---|---|---|
| 4,119,532 A | * | 10/1978 | Park | ..................... | B03B 5/623 |
| | | | | | 209/159 |
| 4,777,444 A | * | 10/1988 | Beijk | ................. | G01N 27/4165 |
| | | | | | 204/401 |
| 4,822,456 A | * | 4/1989 | Bryan | ................. | G01N 27/4165 |
| | | | | | 204/412 |

(Continued)

FOREIGN PATENT DOCUMENTS

CN 201119871 Y 9/2008

OTHER PUBLICATIONS

Int'l Search Report and Written Opinion issued Nov. 11, 2015 in Int'l Application No. PCT/US2015/041680.

(Continued)

*Primary Examiner* — Jean R Jeanglaude
(74) *Attorney, Agent, or Firm* — Panitch Schwarze Belisario & Nadel LLP

(57) ABSTRACT

A sensing circuit for an electrochemical sensor includes a digital-to-analog converter (DAC), an operational amplifier, an instrumentation amplifier, and an analog-to-digital converter (ADC). The DAC generates a biased ground voltage signal which is received by the operational amplifier. The operational amplifier creates a high current biased voltage on one of a pair of terminals connected to the electrochemical sensor. The instrumentation amplifier receives a signal from the pair of terminals, and generates an output representative of a voltage across the pair of terminals with reference to the high current biased ground voltage signal. The ADC converter receives the output and derives an actual voltage reading taken by the electrochemical sensor.

26 Claims, 3 Drawing Sheets

(56) References Cited

U.S. PATENT DOCUMENTS

2005/0247576 A1 11/2005 Tom et al.
2009/0157338 A1 6/2009 Wang

OTHER PUBLICATIONS

Wang et al., "Real-Time Telemetry System for Amperometric and Potentiometric Electrochemical Sensors," Sensors, vol. 11, No. 12, pp. 8593-8610 (2011).
"AN-1852 Designing with pH Electrodes," Texas Instruments, Application Report, SNOA529A, Sep. 2008, Revised Apr. 2013.
Seitz, "Designing with pH Electrodes: Application Note AN-1852" Analog edgeSM, National Semiconductor Corporation, (2008).

\* cited by examiner

ELECTROCHEMICAL SENSING MODULE

CROSS-REFERENCE TO RELATED APPLICATIONS

This application claims the benefit of U.S. Provisional Patent Application No. 62/028,469, filed on Jul. 24, 2014, entitled "Electrochemical Sensing Module," the entire contents of which are incorporated herein by reference in their entirety.

BACKGROUND OF THE INVENTION

Embodiments of the present invention relate to electrochemical sensors, and more particularly, to a sensing circuit for an electrochemical sensor.

High end sensors for measuring a hydrogen concentration, or a pH value, of a fluid, in which the sensor is submerged have existed for some time. However, effective digital measurement using such devices can be challenging. For example, typical probes used on a pH circuit generate voltages on the order of a few millivolts to several hundred millivolts. Such probes can also generate negative voltages which are problematic because, most analog to digital converters (ADCs) used to perform most digital measurements, are not equipped to measure negative voltages. As such, for effective digital measurement, a system's analog front end (AFE) should be designed to not present the ADC with a negative voltage. Through signal conditioning, it is also desirable for the system to use most, if not all, of the dynamic range of the ADC, as well as filter and/or suppress noise presented to the ADC.

To ensure the dynamic range of the ADC is most effectively used, typical circuits will introduce gain in the AFE section of the circuit. This typically presents several problems, such as a) the gain introduces noise, b) the gain introduces other error (e.g., input offset current gain and other gain nonlinearities), and c) the gain must be variable to effectively condition a wide variety of signals.

It is therefore desirable to provide a sensing circuit for an electrochemical sensor that enables use of most of the dynamic range of the ADC, increases sensitivity and accuracy, and provides data in a digital form that can be transferred and utilized by further systems.

SUMMARY OF INVENTION

Embodiments of the present invention include a sensing circuit for an electrochemical sensor. The sensing circuit includes a digital-to-analog converter (DAC), an operational amplifier, an instrumentation amplifier, and an analog-to-digital converter (ADC). The DAC generates a biased ground voltage signal which is received by the operational amplifier. The operational amplifier creates a low current biased voltage on one of a pair of terminals connected to the electrochemical sensor. The instrumentation amplifier receives a signal from the pair of terminals, and generates an output representative of a voltage across the pair of terminals with reference to the high current biased ground voltage signal. The ADC converter receives the output and derives an actual voltage reading taken by the electrochemical sensor.

BRIEF DESCRIPTION OF THE DRAWINGS

The following detailed description of a preferred embodiment of the invention, will be better understood when read in conjunction with the appended drawings. For the purpose of illustration, there is shown in the drawings an embodiment which is presently preferred. It should be understood, however, that the invention is not limited to the precise arrangements and instrumentalities shown.

DETAILED DESCRIPTION OF THE INVENTION

Figure 1:
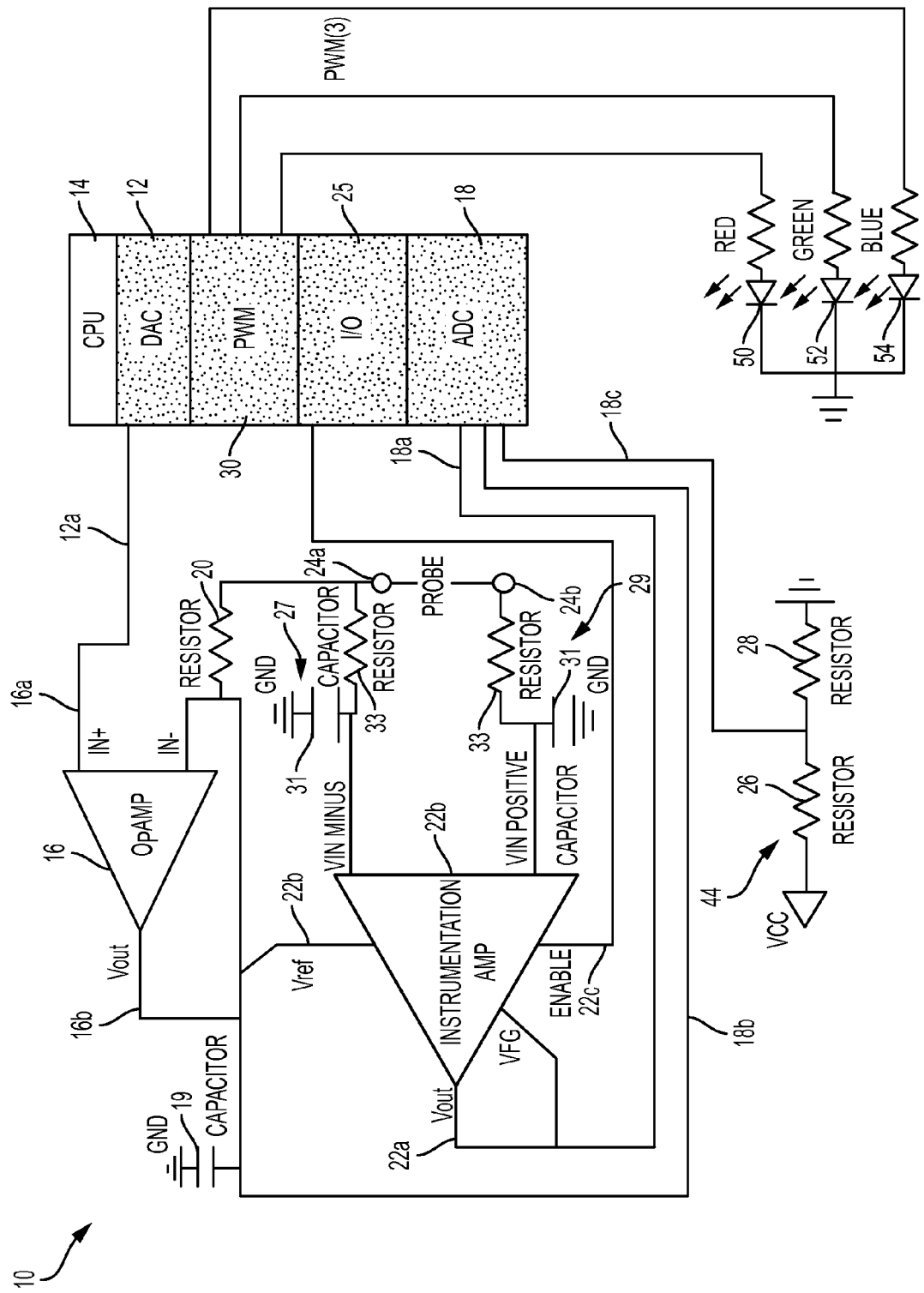
FIG. 1 is a schematic view of a sensing circuit in accordance with a preferred embodiment of the present invention.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof The terminology includes the above-listed words, derivatives thereof, and words of similar import. Additionally, the words "a" and "an", as used in the claims and in the corresponding portions of the specification, mean "at least one."

Embodiments of the present invention address the above discussed challenges by using variable references for an ADC instead of gain. By way of non-limiting example, a pH probe may have an effective range of −200 mV to +200 mV (for a total dynamic range of 400 mV).

Instead of gaining this via an amplifier, a sensing circuit may instead use a 0.512V reference for the ADC, which contains the 400 mV of dynamic range needed for the signal. Using oversampling techniques, it is possible to sample this signal at a 16 bit resolution, yielding an effective 8μV resolution which allows for 51,200 distinct ADC states for the 400 mV range of the probe. The ability to change references effectively replaces the gain stage, allowing for a simpler circuit which utilizes the maximum capabilities of today's integrated CPUs.

Referring to the drawings, wherein like numerals indicate like elements throughout, there is shown in FIG. 1 a sensing circuit 10 for use with an electrochemical sensor (not shown) in accordance with a preferred embodiment of the present invention. An electrochemical sensor can be thought of as a very weak battery. For example, an electrochemical sensor, such as a pH probe, acts as a simple single cell battery with a very high resistance where the voltage produced is proportional to the hydrogen ion concentration around that probe, and therefore proportional to the Log of the hydrogen ion concentration. The produced voltage can be positive or negative depending on, for example, the pH of the solution being measured, and can be as low as a microvolt or as high as many volts. The source impedance of a typical pH probe is very high because the thin glass bulb has a large resistance which is typically in the range of 10 M ohms (Ω) to 10 GΩ. Important sensor characteristics need to be accounted for in order to design a circuit that will condition the sensor signal so that it can be properly utilized by other components (such as an analog-to-digital converter (ADC), CPU, and the like) along the signal path.

Because many electrochemical sensors produce a bipolar signal and most applications operate on a single supply, embodiments of the present invention shift the signal. As such, the circuit 10 includes a digital-to-analog converter (DAC) unit 12 programmed by a CPU 14 to generate a biased output signal 12a of a desired voltage. The current of the biased output 12a may be too weak for an artificial ground. As such, the biased output 12a is coupled to a non-inverting input 16a of an operational amplifier 16. Configured as a voltage follower, the operational amplifier 16 generates an output 16b that "follows" (e.g., matches) the voltage of the non-inverting input 16a. Further, because of a voltage follower's characteristically high input impedance and low output impedance, the operational amplifier 16 outputs a current that is greater than that of the current at the non-inverting input 16a of the operational amplifier 16. As discussed above, the signal output from the DAC unit 12 has a very low current. However, after operation through the operational amplifier 16, the output 16b now has a high enough current to be used by the rest of the sensing circuit 10.

The operational amplifier output 16b is coupled to an input 18b of an analog-to-digital converter (ADC) unit 18, a reference voltage 22b of an instrumentation amplifier 22, as well as to a ground pin 38 (shown in FIG. 2) of the electrochemical sensor, which becomes the biased ground voltage. Thus, in effect, this biased ground voltage serves to shift the bipolar electrochemical sensor signal to a unipolar signal, which can be used, for example, with a single-supply system (e.g., a system able to only read positive voltages). To remove noise on the biased ground voltage, a decoupling capacitor 19 is coupled to the output 16b of the operation amplifier 16. The capacitor 19 preferably has a capacitance of 1 Nano farad. However, other capacitances may be used as well in keeping with the invention. Because electrochemical sensors are highly sensitive to electric current, the operational amplifier output 16b is coupled to ground via a current limiting resistor 20. The current limiting resistor 20 preferably has a resistance of 100 ($\Omega$). However, other resistances may be used as well in keeping with the invention.

The instrumentation amplifier 22 has inputs connected across a pair of terminals 24a, 24b to which the sensor (not shown) is connected. The terminals 24a, 24b may comprise posts, sockets, coaxial receptacles or the like types of electrical connectors. The terminal 24a represents the biased voltage, while terminal 24b is the voltage that the electrochemical sensor is reading. In an effort to remove any low frequency noise from incoming signals of the probe, low pass filters 27 and 29 are connected to terminals 24a and 24b respectively. Each of the low pass filters 27 and 29 includes a capacitor 31 and a resistor 33. The capacitor 31 preferably has a capacitance of 1 Nano farad, and the resistor 33 preferably has a resistance of 1 k$\Omega$. Because the ground voltage is biased, the output from the probe will be in reference to this biased voltage.

For example, if the biased ground voltage is set to 100 mV, and the probe is reading 5 mV, the output from the probe across the terminals 24a, 24b into the instrumentation amplifier 22 would be 105 mV. As another example, if the biased ground voltage is set to 100 mV, and the probe is reading −5 mV, the output from the probe across the terminals into the instrumentation 22 amplifier would be 95 mV.

The voltage differential generated by the electrochemical sensor is extremely small (e.g., in the millivolt range—ideally 59.16 millivolts per pH unit at room temperature) and has almost no usable current. As such, any measurement device used may need to be very sensitive. Accordingly, embodiments of the present invention employ the instrumentation amplifier 22 to read such a small voltage, but not consume it. For example, the instrumentation amplifier 22 receives, as input, the output voltage from the probe across the terminals 24a, 24b, and determines a difference between the output voltage and the biased ground value. The instrumentation amplifier 22 also receives a signal output by an input/output (I/O) unit 25 as an enable input 22c. The instrumentation amplifier 22 then adds this difference back to the biased ground voltage value, thus generating an output 22a having a value similar to that shown at its input. As such, the instrumentation amplifier 22 insures that the incoming voltage from the probe is accurately and properly referenced to the biased ground.

The output 22a of the instrumentation amplifier 22 is fed back to an input 18a of the ADC 18, which further includes, as input, the biased voltage output 18b from the operational amplifier 16 and a supply voltage signal 18c output from a voltage divider circuit 44 comprising two resistors, 26 and 28, preferably having resistance values of 10 k$\Omega$ and 100 k$\Omega$, respectively. However, it should be noted that the configuration of these resistors is irrelevant. For example, resistor 26 can have a resistance value of 10 k$\Omega$ and resistor 28 can have a resistance value of 100 k$\Omega$. For diagnostic purposes, the voltage divider circuit 44 determines the voltage at which the sensing module circuit has been powered. By subtracting the biased voltage from the instrumentation amplifier output 22a, the sensing module 10 determines an accurate probe voltage reading, which can then used to derive a desired measurement (e.g., pH, ppm ammonium, or the like) of the aqueous solution.

A pulse width modulator (PWM) unit 30, the I/O unit 25, and the ADC 18 are preferably part of, or at least controlled by, the CPU 14. The CPU 14 may be a microcontroller, a microprocessor, application specific integrated circuit (ASIC), or the like. For example, one or more of the PWM unit 30, the I/O unit 25, and the ADC 18 may reside within the CPU 14 such that the inputs and outputs described above may be in the form of pins (not shown) of the CPU 14. Still further, one or more of the PWM unit 30, the I/O unit 25, and the ADC 22 may be circuits externally located from the CPU 14 and may be coupled thereto via traces, wires, or other like electrical connectors (not shown). The CPU 14, for example, may control power supplied, settings and parameters, and facilitate communications for the PWM unit 30, the I/O unit 25, and the ADC 18.

It is preferred that at least the operation amplifier 16, the instrumentation amplifier 22, the current limiting resistor 20, the voltage divider circuit 44, and the terminals 24a, 24b are commonly housed. The housing (not shown) may also contain the PWM unit 30, the I/O unit 25, the ADC 18 and/or the CPU 14, as desired.

Figure 2:
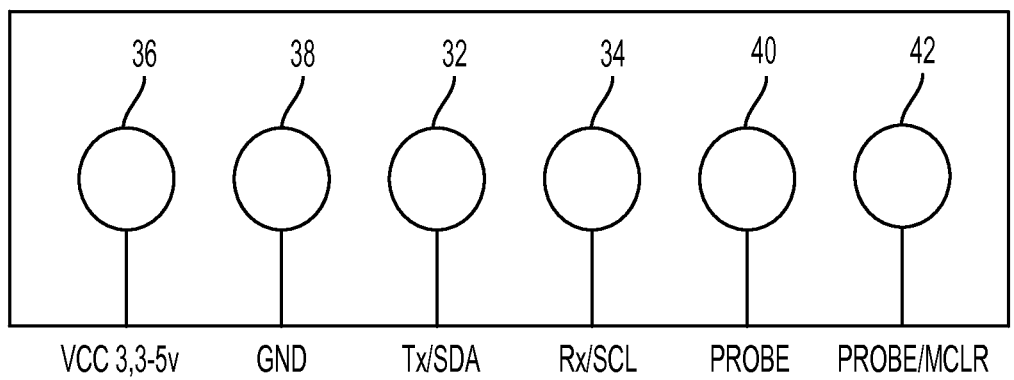
FIG. 2 is a schematic view of a header pin arrangement for the circuit of FIG. 1.

The data obtained from the sensor is preferably passed from the circuit 10 to an external circuit (not shown) using common methods, such as universal asynchronous receiver/transmitter (UART) protocols (e.g., RS-232, TTL serial, RS-422, RS-485, or the like), inter-integrated circuit (I$^2$C) protocol, or the like. Referring to FIG. 2, a pair of transmitter and receiver pins 32, 34 are preferably provided to enable communication with the external circuit, as described above. Power and ground pins 36, 38 may also be provided. In addition, probe pins 40, 42 may be provided for connecting the sensor to the terminals 26a, 26b.

Referring again to FIG. 1, LEDs 50, 52, 54 are preferably provided for indicating a status of the circuit 10 to the user. For example, a red LED 50 may be provided as an error indicator. A green LED 52 may be provided to indicate that communication is occurring pursuant to a UART protocol. Similarly, a blue LED 54 may be provided to indicate that communication is occurring pursuant to I²C. Although LEDs are used in the embodiment shown, other types of indicators, including alphanumeric displays, aural indicators, or the like may also be used. In addition, other conditions of the device 10 and/or the sensor may be communicated to the user.

Embodiments of the present invention provide simple noise rejection via common LPF (LOW PASS FILTER) circuitry and notch filters, to reject common sources of noise and interference such as 60 Hz hum and certain common mode noises. Signals input to the ADC may still have random noise associated with them, albeit low magnitude noise, and this noise is used to the advantage of modern ADC sampling techniques. In order to oversample an ADC reading, it is desirable that the signal under measurement contain noise classified as "white noise", which implies the power density of the spectrum of the signal is constant within the range measurable by the ADC. Maintaining such noise (which can be caused by EMI, thermal noise, chemical noise, as well as other sources), aids the microprocessor's ability to oversample the signal. Thus, the 10 or 12 bit ADCs on today's embedded microprocessors can easily be extended upwards to 4-6 bits to allow a higher resolution sample to be taken. Further digital processing techniques (such as LPF and other averaging schemes) allow precise and high resolution measurements to be taken, with no complex AFE circuitry, thus maximizing the use of the microprocessor's capabilities.

Embodiments of the present invention may employ a multi-layer printed circuit board to mechanically support and connect the above discussed electrical components, preferably with gold-plated leads. As evidenced from above, sections of the sensing circuit use an artificial biased ground and others use a real ground. Accordingly, the section of the circuit using the artificial ground has a layer of the multi-layer PCB that is a ground plane connected to the artificial biased ground. Likewise, the section of the circuit that uses the real ground has a layer of the PCB that is a ground plane connected to the real ground.

Figure 3:
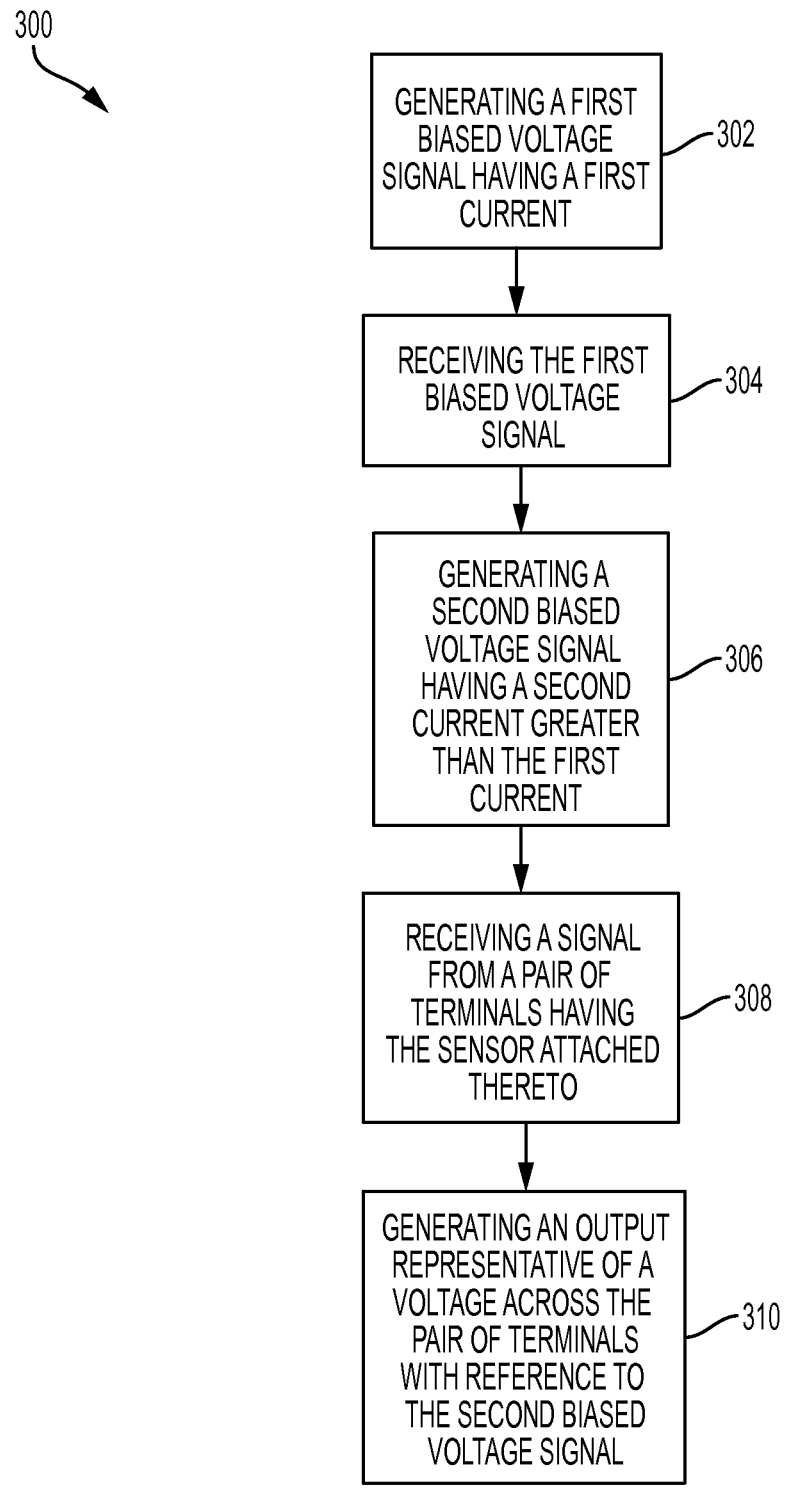
FIG. 3 is a flow diagram of a method for deriving a reading from a sensor according to an embodiment of the present invention.

FIG. 3 is a flow diagram of one embodiment of a method 300 for deriving a reading from a sensor. The method 300 may comprise a number of steps which may be performed in any suitable order. Step 302 comprises generating a first biased voltage signal having a first current. Step 304 comprises receiving the first biased voltage signal. Step 306 comprises generating a second biased voltage signal having a second current greater than the first current. This second biased voltage signal may be used by other components of the sensing circuit. Step 308 comprises receiving a signal from a pair of terminals having the sensor attached thereto. Step 310 comprises generating an output representative of a voltage across the pair of terminals with reference to the second biased voltage signal.

From the foregoing, it can be seen that embodiments of the present invention comprise sensing circuits for electrochemical sensors. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sensing circuit for a sensor, the circuit comprising:
 a digital-to-analog converter (DAC) configured to generate a first biased voltage signal having a first current;
 an operational amplifier configured to:
  receive the first biased voltage signal; and
  generate a second biased voltage signal having a second current greater than the first current;
 an instrumentation amplifier configured to:
  receive a signal from a pair of terminals having the sensor attached thereto; and
  generate an output representative of a voltage across the pair of terminals with reference to the second biased voltage signal; and
 an analog-to-digital converter (ADC) configured to derive, using the output, a sensor voltage read from the sensor.

2. The sensing circuit of claim 1, wherein the sensor voltage is derived by subtraction of the second biased voltage signal from the output.

3. The sensing circuit of claim 1, further comprising one or more indicators configured to indicate an operating status of the sensing circuit.

4. The sensing circuit of claim 1, further comprising an input/output unit configured to generate an enable input for the instrumentation amplifier.

5. The sensing circuit of claim 4, further comprising a processor configured to control at least one of the instrumentation amplifier, the input/output unit, and the ADC.

6. The sensing circuit of claim 1, further comprising a transceiver configured to communicate the sensor voltage to a circuit remote to the sensing circuit.

7. The sensing circuit of claim 1, further comprising a voltage divider circuit configured to determine a voltage at which the sensing circuit is powered.

8. The sensing circuit of claim 1, wherein the first biased voltage signal is variable, and wherein the sensing circuit further comprises a processor configured to program the DAC to generate the first biased voltage signal with a value that is programmed by the processor based on an application of the sensing circuit, wherein the sensing circuit is not limited to one type of application.

9. The sensing circuit of claim 1, wherein the instrumentation amplifier is configured to receive, as a distinct input, the second biased voltage signal.

10. A sensing circuit for a sensor, the circuit comprising:
 a digital-to-analog converter (DAC) configured to generate a first biased voltage signal having a first current;
 an operational amplifier configured to:
  receive the first biased voltage signal; and
  generate a second biased voltage signal having a second current greater than the first current;
 an instrumentation amplifier configured to:
  receive a signal from a pair of terminals having the sensor attached thereto; and
  generate an output representative of a voltage across the pair of terminals with reference to a biased ground voltage signal; and
 an analog-to-digital converter (ADC) configured to derive, by subtracting the second biased voltage signal from the output, a sensor voltage read from the sensor.

11. The sensing circuit of claim 10, further comprising one or more indicators configured to indicate an operating status of the sensing circuit.

12. The sensing circuit of claim 10, further comprising a transceiver configured to communicate the sensor voltage to a circuit remote to the sensing circuit.

13. The sensing circuit of claim 10, further comprising a voltage divider circuit configured to determine a voltage at which the sensing circuit is powered.

14. The sensing circuit of claim 13, wherein at least two of the operation amplifier, the instrumentation amplifier, the voltage divider circuit, and the processor are commonly housed.

15. The sensing circuit of claim 10, further comprising a low pass filter configured to filter noise associated with the output.

16. The sensing circuit of claim 10, further comprising an input/output unit configured to generate an enable input for the instrumentation amplifier.

17. The sensing circuit of claim 16, further comprising a processor configured to control at least one of the instrumentation amplifier, the input/output unit, and the ADC.

18. The sensing circuit of claim 10, wherein the first biased voltage signal is variable, and wherein the sensing circuit further comprises a processor configured to program the DAC to generate the first biased voltage signal with a value that is programmed by the processor based on an application of the sensing circuit, wherein the sensing circuit is not limited to one type of application.

19. The sensing circuit of claim 10, wherein the instrumentation amplifier is configured to receive, as a distinct input, the second biased voltage signal.

20. A method for deriving, using a sensing circuit, a reading from a sensor, the method comprising:
    generating, by a digital-to-analog converter (DAC), a first biased voltage signal having a first current;
    receiving, by an operational amplifier, the first biased voltage signal;
    generating, by the operational amplifier, a second biased voltage signal having a second current greater than the first current;
    receiving, by an instrumentation amplifier, a signal from a pair of terminals having the sensor attached thereto;
    generating, by the instrumentation amplifier, an output representative of a voltage across the pair of terminals with reference to the second biased voltage signal; and
    deriving, by an analog-to-digital converter (ADC), a sensor voltage read from the sensor.

21. The method of claim 20, wherein deriving the sensor voltage comprises subtracting the second biased voltage signal from the output.

22. The method of claim 20, further comprising providing an indication of an operating status of the sensing circuit.

23. The method of claim 20, further comprising communicating the sensor voltage to a circuit remote to the sensing circuit.

24. The method of claim 20, further comprising filtering noise associated with the output.

25. The method of claim 20, wherein the first biased voltage signal is variable, and wherein the method further comprises programming, by a processor, the DAC to generate the first biased voltage signal with a value that is programmed by the processor based on an application of the sensing circuit, wherein the sensing circuit is not limited to one type of application.

26. The method of claim 20, further comprising receiving, by the instrumentation amplifier, the second biased voltage signal, as a distinct input to the instrumentation amplifier.

* * * * *